(12) United States Patent
Schlagheck et al.

(10) Patent No.: US 7,996,066 B2
(45) Date of Patent: Aug. 9, 2011

(54) TOPOGRAPHIC OPTICAL INFRARED TOMOGRAPHY SYSTEM FOR BIOPHYSICAL IMAGING WITH INFRARED DIAGNOSTIC EXPLORATORY ALGORITHM SEQUENCING (IDEAS) SCRIPTING LANGUAGE

(75) Inventors: Jerry Schlagheck, West Chester, OH (US); T Randall Lane, Lebanon, OH (US)

(73) Assignee: New Frontier Imaging LLC, Dayton, OH (US)

( * ) Notice: Subject to any disclaimer, the term of this patent is extended or adjusted under 35 U.S.C. 154(b) by 597 days.

(21) Appl. No.: 11/839,667

(22) Filed: Aug. 16, 2007

(65) Prior Publication Data
US 2009/0048523 A1    Feb. 19, 2009

(51) Int. Cl.
  *A61B 6/00* (2006.01)
  *A61B 5/00* (2006.01)
  *G02B 26/10* (2006.01)

(52) U.S. Cl. ........ 600/474; 600/549; 250/332; 250/334; 250/316.1

(58) Field of Classification Search .................. 600/473, 600/425, 476, 474; 250/332, 334, 316.1
See application file for complete search history.

(56) References Cited

U.S. PATENT DOCUMENTS

| | | | | |
|---|---|---|---|---|
| 4,691,712 A | * | 9/1987 | Brown, Jr. ...................... | 600/549 |
| 5,444,241 A | * | 8/1995 | Del Grande et al. .......... | 250/253 |
| 5,492,122 A | * | 2/1996 | Button et al. ................. | 600/411 |
| 5,808,303 A | * | 9/1998 | Schlagheck et al. .......... | 250/330 |
| 6,438,255 B1 | * | 8/2002 | Lesniak ....................... | 382/107 |
| 6,442,419 B1 | * | 8/2002 | Chu et al. ...................... | 600/474 |
| 7,292,719 B2 | * | 11/2007 | Arnon ........................... | 382/128 |
| 2006/0232675 A1 | * | 10/2006 | Chamberlain et al. ........ | 348/164 |

* cited by examiner

*Primary Examiner* — Long V Le
*Assistant Examiner* — Helene Bor
(74) *Attorney, Agent, or Firm* — R. William Graham (57) ABSTRACT

A topographic optical infrared tomography system for biophysical imaging includes a thermal camera operably disposed adjacent a body part equipped for obtaining thermal data readings from the body part and apparatus operably connected to the thermal camera for correcting thermal emissivity variations in the thermal data readings to provide corrected thermal data. A method for obtaining physiological data using the thermally corrected data is also provided.

15 Claims, 10 Drawing Sheets

FIG. 3 Top View    FIG. 4 Side View    FIG. 5 End View

Top View  
FIG. 9

Side View  
FIG. 10

$$\text{Modulation Transfer Function} = \frac{I_{max} - I_{min}}{I_{max} + I_{min}}$$

TOPOGRAPHIC OPTICAL INFRARED TOMOGRAPHY SYSTEM FOR BIOPHYSICAL IMAGING WITH INFRARED DIAGNOSTIC EXPLORATORY ALGORITHM SEQUENCING (IDEAS) SCRIPTING LANGUAGE

FIELD OF INVENTION

The present invention relates to the field of medical screening procedures. More particularly, the present invention relates to a biophysical imaging system employing an infrared camera, visual camera, laser and associated mathematical and physical software and hardware to perform advanced biophysical tissue screening.

BACKGROUND OF THE INVENTION

In the medical field, screening tests are used to evaluate a population of people for a specific disease without anyone being known as having any symptoms or signs related to the specific disease for which they are being tested. In other words, a screening test hunts for a disease before it starts producing any symptoms. There are numerous techniques which exist in the field for examining physiology of a patient for screening purposes.

With respect to certain cancers, such as breast cancer which is the second leading cause of cancer deaths in women today, the most accepted testing procedure remains mammography with about 44 million procedures and 1.2 million breast biopsies performed in the United States a year. This is an invasive and painful procedure and although fairly reliable, does produce false positives and negatives.

The migration and diffusion of energy transfer through tissue is a function its physiological state and tissue properties that can display images of physiological parameters, which can be early markers of tumor/cancer development. Cancerous regions within normal tissue display substantially different physiology from normal tissue due to their primitive cell physiology. These abnormal regions have angiogenesis and higher degrees of metabolic rates when compared to normal tissue. The physiological differences will result in a change in thermal activity that can be detected and measured in tomographic data.

Thermal screening of the human body has been employed for many years as a means to screen for abnormalities in humans and animals. Thermal screening, much like x-ray (mammograms) screening, is an interpretation of the image data, performed by a skilled person, based on densities, physical characteristics and location in the case of x-rays or thermal patterns in the case of thermographic screening. In the case of x-ray screening, the determination to start this process is based on a risk/benefit of the procedure as x-ray employs ionizing radiation as a means for deriving the image that is cumulative within tissue and can damage DNA strands resulting in abnormal tissue growth. Tomography is a technique using ultrasound, gamma rays, or X-rays to produce a focused image of structures across a certain depth within the body, while blurring details at other depths of the body. A topographic image is traditionally associated with a mapping technique that displays elevation and contour.

Thermographic screening has the benefit of being a totally passive technology however the current techniques and methodologies lack effectiveness. In the case of the mammary gland, metabolic changes result in increased thermal activity in the gland during the menstruation cycle. A deficiency of thermographic imaging is the requirement that infrared radiation be observed at angles normal to the surface when viewed by the thermal array as thermal radiation is normal to the surface. This requires multiple images of the area being observed and repositioning the thermal array. Consequently, thermal acquisition errors result due to the off angle of the energy being emitted. Depending on the geometry of the area being imaged the off angle radiation can be substantial.

The present invention addresses the need for a controlled environment, emissivity corrections and actual tissue relating to body mass. At present this biophysical imaging technique is performed in a two dimensional world. However, when imaging the human body's infrared radiation and measuring the heat transfer we are attempting to solve a three-dimensional problem in a two dimensional world. Currently, there has not been produced a way for processing the observed data at a theoretical and primary level. Without question all current thermal imaging techniques are flawed.

There remains a need for a less invasive yet more reliable screen testing procedure for certain physiological tissue such as cancers, particularly breast cancer.

SUMMARY OF THE INVENTION

The instant invention provides a device and method for translating an acquired thermal image into a three dimensional thermal map. The invention provides a first step in true and precise medical thermal imaging. The invention provides for simulating thermal conductive of tissue in a full three dimensional array rendering the system as being one of the most advanced techniques possible. This is done by employing algorithm analysis techniques such as the Pennes equation. By using a Digital Imaging and Communications in Medicine (DICOM) format (a format for international standards for the communication of biomedical, diagnostic and therapeutic information in those medical disciplines that use digital images and associated data a standard developed by the American College of Radiology Manufacturers Association to define the connectivity and communication protocols of medical imaging devices), the present invention provides the possibilities of merging thermal technology with digital X-ray, CAT and MRI data. By applying thermal data to the current imaging technologies, the invention provides a significant leap forward in medical science.

Infrared Diagnostic Exploratory Algorithm Sequencing (IDEAS) is a scriptable language developed specifically for the present invention that uses unique algorithms and processes for the present system. The system of the invention provides for an assortment of imaging applications, even small animal testing.

The instant invention also provides for analysis of Moiré patterns (patterns produced by interference of a series of periodically arranged linear light sources wherein a line-specimen grating of similar pitch are located at a plane parallel to the sources and the specimen grating and at some distance away from these planes, or an interference pattern is created, for example, when two grids are overlaid at an angle, or when they have slightly different mesh sizes). Moiré patterns are often an undesired artifact of images produced by various digital imaging and computer graphics techniques, for example when scanning a halftone picture or ray tracing a checkered plane. A transparent or reflecting specimen located at a distance from the specimen grating distorts the image of the multisource projected on the specimen grating due to its surface irregularities and forms a Moiré pattern. This pattern yields the partial-slope contours of the topography of the specimen along a direction normal to the lines of the grating.

Two such contour patterns taken at mutually perpendicular directions are sufficient to yield the complete topographic picture of the surface.

The topographic optical infrared tomography for biophysical imaging system of the instant invention is a passive, painless and non-invasive screening system which can determine the changes in temperature (metabolic) that precede the structure change in tissue leading to a possible early detection of breast cancer by years when compared to current procedures. The current topographic optical infrared tomography system for biophysical imaging overcomes the current barriers to widespread x-ray mammography, including dense tissue and age of subject. Thermal imaging eliminates the risks related to x-ray screening. Thermal imaging as used in the instant invention provides the ability to detect small tumors several years earlier (potentially, before they can metastasize), without exposure to x-rays and discomfort during testing procedure. The topographic optical infrared tomography system for biophysical imaging has the potential to deliver a substantially more accurate, less expensive, non-invasive, easier to use diagnostic test for biological tissue, such as breast cancer and other conditions, offering the hope of saving many patients lives through earlier detection of breast cancer, while at the same time lowering the overall cost of healthcare delivery.

Measurements of metabolic activity such as thermal changes as diffused through tissue can be used by the instant invention to calculate and reconstruct images of internal biophysical properties. Thermal fluid dynamics modeling combined with topographic correction modeling of the surface a propagation of thermal activity in tissue can be used to calculate maps of thermal changes within the breast, and therefore physiological maps of metabolic rates can be displayed with accuracy in an image for analysis.

The image data acquired is not limited to the screening of cancer. The image data combined with selected embedded procedural algorithms can be used for the analysis of aiding the grafting of skin for burn sufferers, reducing the pueblo effect aiding in pharmaceutical drug chemical reaction analysis and similar biophysical functions.

In the case of burn sufferers where skin grafting is necessary the largest risk of this procedure is the amount of grafting required. By employing the invention, a surgeon performing this procedure determines what is healthy tissue versus dead tissue without any basis that a visual indication. A controlled thermal image of the area of the burn, using the techniques and methodology of the topographic optical infrared tomography system can provide an image of living tissue versus dead tissue.

In the case of pharmaceutical companies testing new drugs, the invention can reduce their test time by acquiring biophysical data in the area that the drug should be interacting. This allows for the pharmaceutical company to validate the effects of their new drugs with data that measures the effects. This technique could reduce the new drug time to market duration as well as saving millions of dollars of clinical trails and studies.

The topographic optical infrared tomography system for biophysical imaging incorporates acquisition and mapping hardware within a thermally controlled environment with advanced imaging methodological with a wide data bank of processing algorithms. These algorithms not only provide for image enhancements the software provides artificial intelligence of detailing and highlighting suspected area of concern(s) that aids the reader of the data in analyzing the acquired data.

Accordingly, an embodiment of the invention is directed to a topographic optical infrared tomography system for biophysical imaging includes a thermal camera operably disposed adjacent a body part equipped for obtaining thermal data readings from the body part and apparatus operably connected to the thermal camera for correcting thermal emissivity variations in the thermal data readings to provide corrected thermal data. A method for obtaining physiological data using the thermally corrected data and providing indication of condition of a body part is also provided.

DETAILED DESCRIPTION OF PREFERRED EMBODIMENTS

The following description contains detailed discussion applicable to the invention as well as information to aid the reader in understanding this technology and the methodology of the system. The information provided should be readily understood by a person skilled in the art.

The topographic optical infrared tomography system for biophysical imaging of the present invention is generally referred to by the numeral 100. The topographic optical infrared tomography system 100 for biophysical imaging includes an imaging device 112 and analysis device 114 that incorporates (1) biophysical characteristics and biophysical stimuli. The imaging device 112 can includes a photon acquisition device, such as an infrared camera having a spectral range of 1.5 to 5 microns or 7 to 16 microns and a visual camera, e.g. a wavelength of about 9 microns can be used but a broader range is contemplated (see Intermediate Physics for Medicine and Biology (third edition), Russell K. Hobbie) and a laser. The analysis device 114 can include a computer based device having an operating system and software for performing a mathematical traditional and/or unique algorithms that are fundamentally based on thermal fluid dynamics but modified for biophysical tissue and metabolic parameters for the construction of metabolic images via such as those as related to Moiré patterns, photon movement and mathematics associated with the Modulation Transfer Function. The entire system modular design (hardware and software) allows for selecting certain techniques and methodologies to a patient, such as only the Post processing/Imaging Enclosure sections of this write-up as an example.

The imaging abilities of the topographic optical infrared tomography system 100 can include a fully functional data base management system for the archival of all acquired images and individual data which can employ a standard SQL database. All pre-processed images are stored in a raw format while all post-processed images are stored in a standard medical DICOM format.

Figure 1:
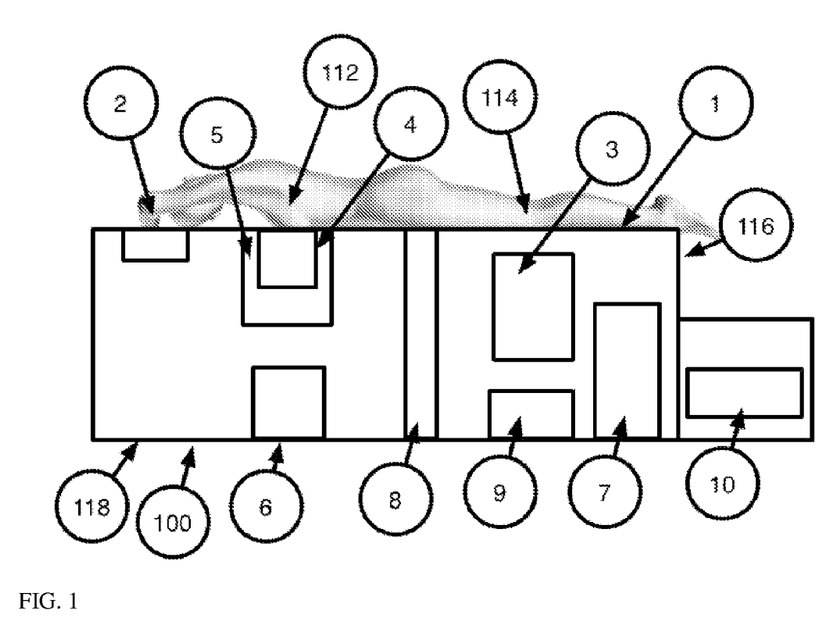
FIG. 1 is a side schematic view illustrating the invention.

The system 100 includes an enclosure (1) which provides for a stable and comfortable platform configured for the subject to lay in a prone position thus minimizing movement during the data acquisition as seen in FIG. 1. The enclosure (1) can be divided into two sections that are separated by a thermal barrier (8). A first section 116 is characterized to include electronic bay and analysis device (114) which houses a liquid chiller (3) which is plumbed to a reservoir (2). The liquid chiller (3) will fill and drain the reservoir (2) at predetermined times under control of a central control computer (7) via the input/output (10) assembly (9).

The system 100 is provided with power via a power junction box (10) that interfaces to a 120V ac power source. The power junction box (10) distributes 120V ac and converts the supplied 120V ac into 12V dc and 24V dc for a visual/infrared/laser (VIL) assembly (6). Exhaust fans (19) can be operably disposed throughout the section (116) (the electronic bay compartment) sidewalls (8) to aid in the cooling of electrical hardware within the section (116).

A second section (118) includes the imaging device (112) and includes walls, particularly inside walls, constructed with a fine carbon/graphic mixture of paint that provides for a heat absorbing capabilities and a non-reflective surface. This paint provides for a high thermal conductivity factor that allows heat to be transferred via the imaging enclosure sidewalls. An imaging control compartment (5) is provided for capturing data from an area of interest.

Figure 2:
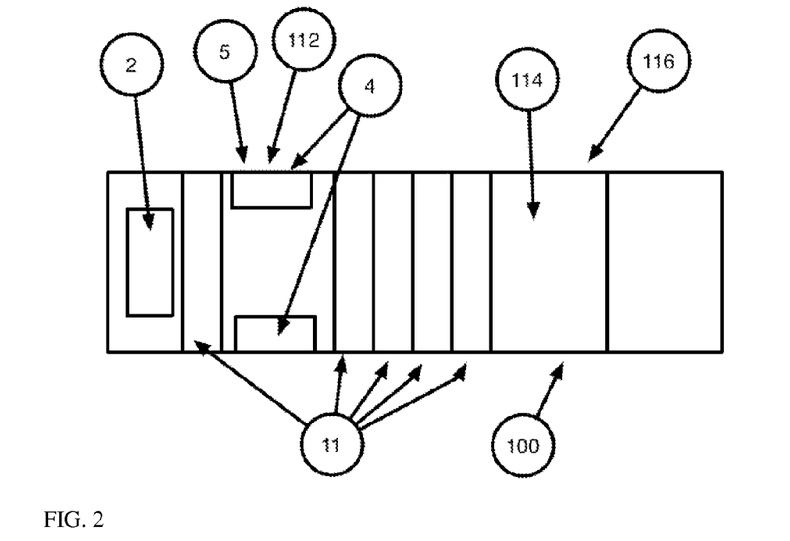
FIG. 2 is top schematic view of the invention.
Figure 3:
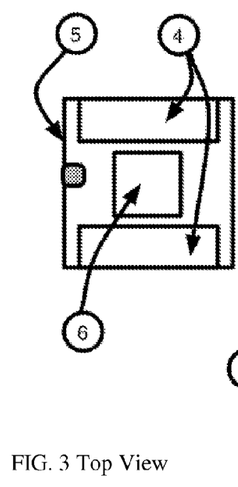
FIG. 3 is a top view of an imaging component of the invention.
Figures 4, 5:
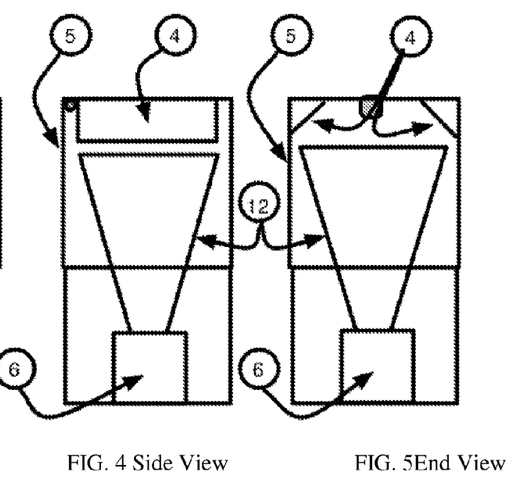
FIG. 4 is a side view of the component in FIG. 3.
FIG. 5 is an end view of the component in FIG. 3.
Figure 9:
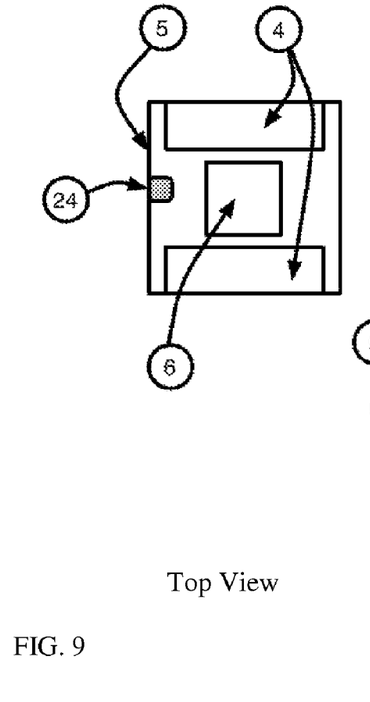
FIG. 9 is another top view of an imaging compartment of the invention with a blackbody therein.
Figure 10:
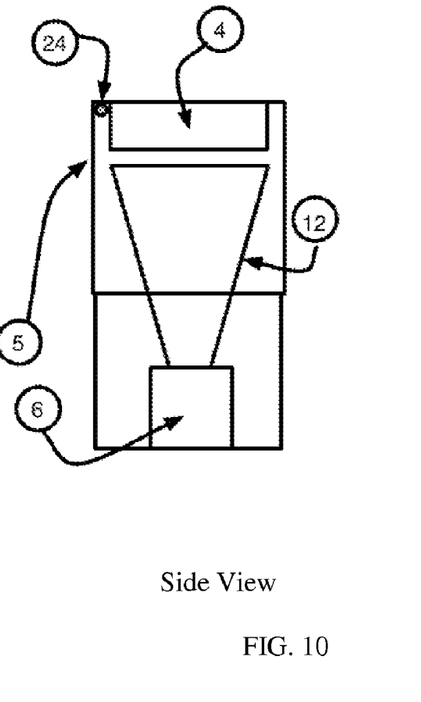
FIG. 10 is side view of the imaging compartment in FIG. 9.

Referring to FIG. 2, the imaging enclosure (1) has a top surface constructed with removable and re-positional panels (11). These removable and re-positional panels (11) allow for the movement of the imaging control compartment (5) to be positioned at different locations allowing for image acquisition of different organs/locations of the human body. The imaging control compartment (5) is associated with the VIL assembly (6) and are collectively movable such the imaging control compartment (5) and the VIL assembly (6) are in their desired alignment as seen in FIGS. 9 and 10, for example.

The imaging control compartment (5) includes four walls with the top and bottom open. Two front downward facing surface mirrors (4) are attached to the imaging control compartment (5) and are equipped to be disposed at adjustable angles via a pivot connection to provide the ability for the VIL assembly (6) and its components to acquire data during an image acquisition process. The field of view of cameras and laser projections (12) covers the entire area of imaging interest. The imaging control compartment (5) is coated with the same conductive paint on all surfaces and is attached to the VIL assembly (6) with brackets on the four corners. The brackets and the external surfaces of the VIL assembly (6) are also coated with the same conductive paint.

Figure 6:
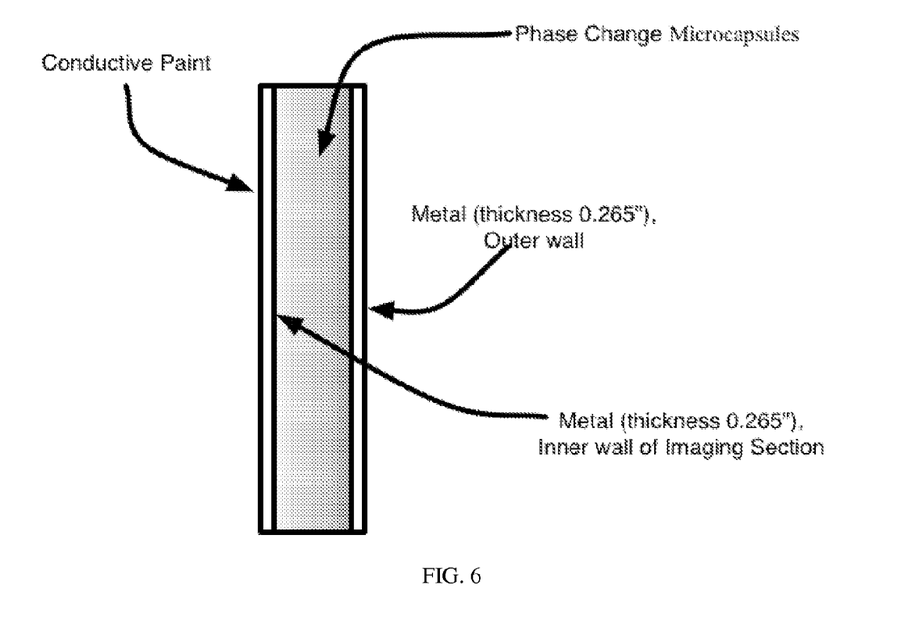
FIG. 6 illustrates a section of a part of a wall component of the invention.
Figure 7:
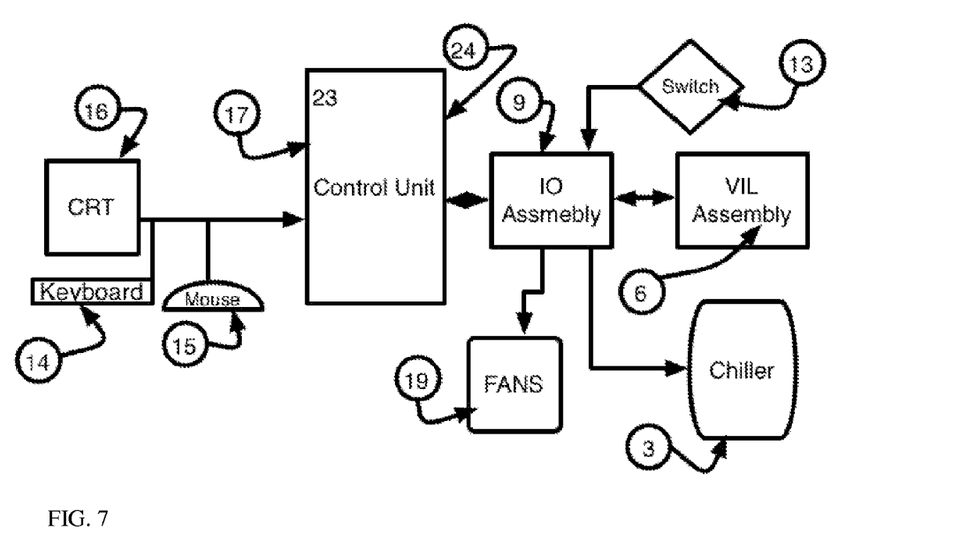
FIG. 7 illustrates an operational schematic of the invention.

Between the imaging control compartment (5) and electronic bay section (116), the thermal barrier (8) contains fans (19) that pull air from the section (118) into the electronic bay section (116) for temperature control. During the imaging process, these fans (19) have a shutter which closes during this period to eliminate and boundary air flow across any surface of the imaging cavity. When performing thermal imaging any air movement can create unwanted thermal gradients and errors in data reading can be flawed. By eliminating any possible air flow during this process allows for a consistent and reliable thermal image to be acquired. The conductive paint provides a secondary method to reduce any airflow (commonly termed thermals) as the conductive paint absorbs radiated thermal energy and which would otherwise be reflected back into or onto any surfaces. This heat is then exhausted via the fans in the electronic bay to the ambient air of the room. The general construction of the enclosure (1), the thermal barrier (8) and the panels (11) are of a double wall construction. This double wall construction can be made of plastic or metal and eliminates any external hot spots from being absorbed by the structure and then re-radiated within the sections of the enclosure. This double wall construction utilizes the air between the walls to act as an insulator and diffuser. All the external walls, thermal barrier (8) and panels (11) associated with the section 118 of the enclosure (1) are double wall construction and are filled with encapsulated phase change insulating material available from Microtek Laboratories, 5747 Executive Blvd, Dayton, Ohio 45424. Encapsulated phase change materials have the ability to quickly absorb a predefine temperature extreme and re-radiate the per defined temperature keeping the imaging section 118 of the enclosure (1) at a constant temperature without the need for any traditional air conditioning that would create air movements. This double wall construction combined with encapsulated phase change material (as seen in FIG. 6) provides a stabilized thermal imaging enclosure eliminating any possible hot spots that could be radiated to the subject being screened and thus resulting in a flawed reading.

Although thermal imaging has been used for decades in the area of the screening of the human body, to date scientific approaches have been little more than point and shoot and acquire an image. Thermal imaging for breast cancer screening has had some limited success and an assortment of claims on its effective has been published and documented. The use of conventional thermal equipment today overlooks the essential requirement that the area being screened must be totally controlled before thermal data can be truly accurate. Surfaces greater that 45 to 50 degrees appear to have less thermal energy than the surface that is normal to the camera even though the temperature is the same. In the case of breast cancer screening, the observed surfaces commonly exceed these angles.

Current technologies assume that all skin has the same emissivity and that further induces errors in the acquired measurements. However, young skin versus old skin is substantially different in their emissivities as well as skin containing more body fat. To assume that all skin has the same emissivity value is a gross mistake. When taking the aforementioned factors into a cumulative account, one can easily see how substantial errors in the acquired thermal measurements can be seen.

General data is acquired from the subject and entered into the general database of the topographic optical infrared tomography system via a display on a cathode ray tube (CRT) display (16) or the like via a graphical user interface and interaction with the keyboard (14) and mouse (15). The data entered into the database includes, but is not limited to, the subjects name, identification data, and procedure being perform. This general database can be customized for each facility or nation to provide the necessary data fields the users customarily requires. These data records are designed to store image(s) and subject data so that the information can later be recalled for historical viewing and screening.

With the desired procedure defined (in this discussion: breast cancer screening) and the imaging control compartment (5) and panels (11) in position, the subject is instructed to lie still through the data acquisition process. The operator of the topographic optical infrared tomography system (100) via a graphical interface displayed on a CRT (16) initiates the data acquisition process by pressing a switch (13).

Figure 8:
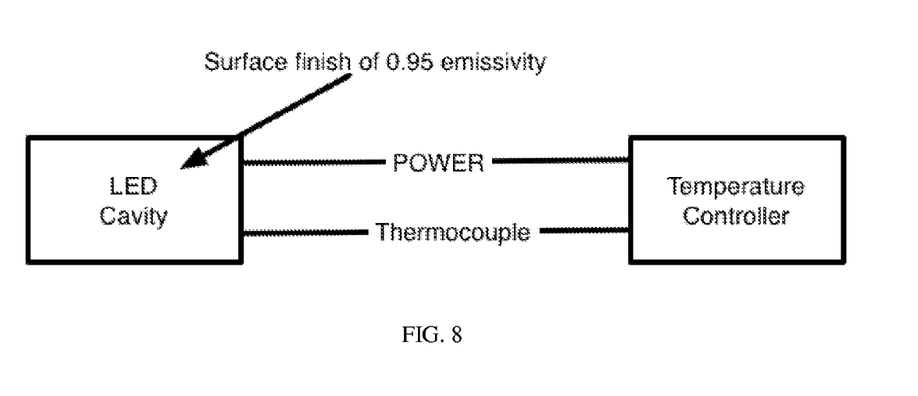
FIG. 8 is a schematic view of a thermocouple component of the invention.

The initiation switch (13) pressed once triggers the IO Assembly (9) to start the data acquisition process controlled by the control unit (7). The control unit (7) sends a message to the CRT (16) that the sequence has started. Pressing the switch (13) at any time during the process will abort the session. The control unit's (7) first task is to signal the IO assembly (9) to turn off the fans (19) and closes the built in shutter. A period of several (e.g., five) seconds elapses to insure an thermally stable imaging environment and the control unit (7) turns on the infrared camera of the VIL assembly (6) and performs a calibration by acquiring a thermal reading from a controlled thermal blackbody (24) termed: Quantum Pulsed Blackbody Cavity (QPBC) (FIG. 8). This QPBC operates at 9.3 microns±0.5 microns. The thermal infrared LED source is packaged in a standard electronic TO-5 packaging (24) to perform the function of a blackbody without introducing a heat element. It does this by the control unit (7) sensing the wavelength of the LED's emission and then calibrating to the anatomy of a person. A blackbody cavity which surrounds the LED is monitored and saved as part of the infrared image during all infrared data collection and integrated in the post processing algorithms. This provides a known temperature in the testing environment.

When measuring humans it is critical that the spectral wavelength being detected by the infrared cameras and the calibration of the camera and blackbody are the same. Slight out of band spectral energy can translate into large thermal temperature errors. Traditional blackbodies radiate at multiple wavelengths ranging for 1 to 18 microns which is a very broad range when attempting to detect thermal differences of less than 0.1 degrees C. The QPBC blackbody radiates at 9.3 microns±0.5 microns for the purpose of biophysical imaging. This wavelength is derived from the standard Human body temperature that is 98.6° F. or 310° K. The wavelength of peak emission (λmax) for humans radiates in accordance with a blackbody (Wiens Law) having a relation:

$$\lambda max = \frac{2,879,800 \text{ nm} \cdot K}{T}$$

The human body temperature in Kelvins (310) in the above relationship:

$$\lambda max = \frac{2,879,800 \text{ nm} \cdot K}{310 K} = 9350 \text{ nm} = 9.35 \text{ microns}$$

Consequently, a general wavelength that a human radiates energy is 9.35 microns.

Figure 11:
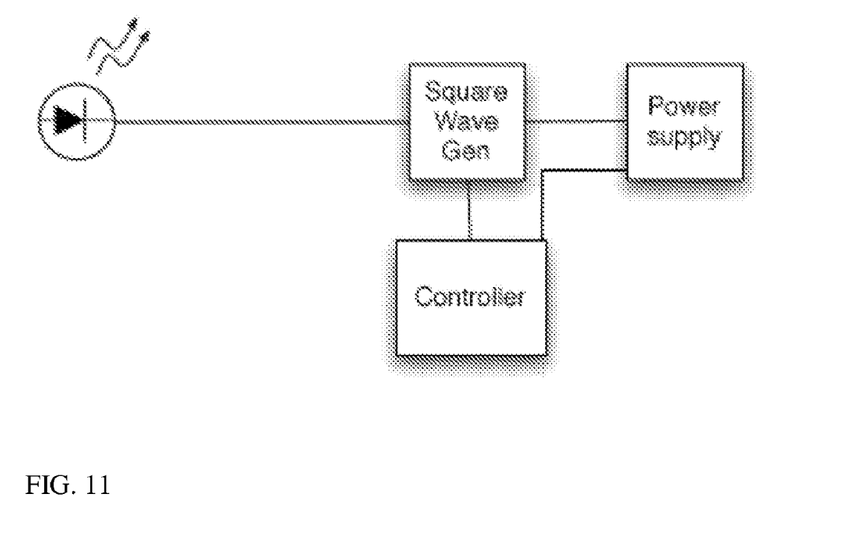
FIG. 11 is a schematic illustrating a controller for the thermal component of the invention.

A blackbody controller (23) which resides in controller (7) monitors and stores an array of temperature readings independently of the data acquired from the thermal imaging camera. In this regard, a thermocouple is attached to the blackbody cavity and is constantly measured via controller (23) assembly to insure there excessive temperature build has not occurred.

Figure 12:
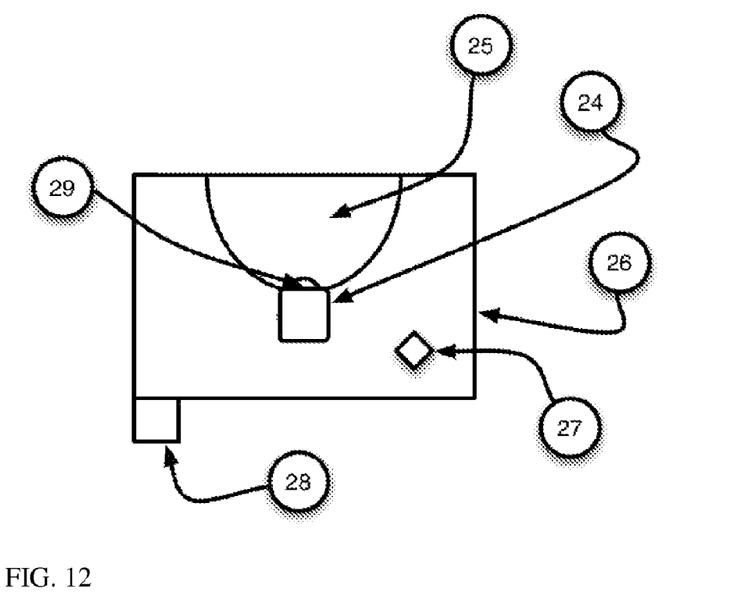
FIG. 12 is a schematic of a blackbody thermocouple of the invention.

The instant blackbody (24) differs from traditional blackbodies which can generate a large amount of heat, air thermals and radiate to surrounding objects. The use of a traditional blackbody would defect the design of the imaging section. The blackbody target calibrator (24) incorporates a tunable infrared emitting diode in both spectral frequency and temperature (duty cycle). A diode is mounted in a 20 degree cavity (25) that provides for detectable and uniform blackbody. The material of the cavity (25) and mounting (26) is metal with a surface finish of the cavity being rough.

A germanium lens (29) that is optically coated to pass 7 to 8 microns is attached to the infrared diode (24). The lens is so designed to radiate to the cavity walls uniformly. A thermal couple is attached to the mounting block to insure that the block is not at an elevated temperature that would induce undesirable radiation. Power, Diode intensity, duty cycle and frequency are controlled via the wiring connection (28) at the base of the assembly.

Figure 13:
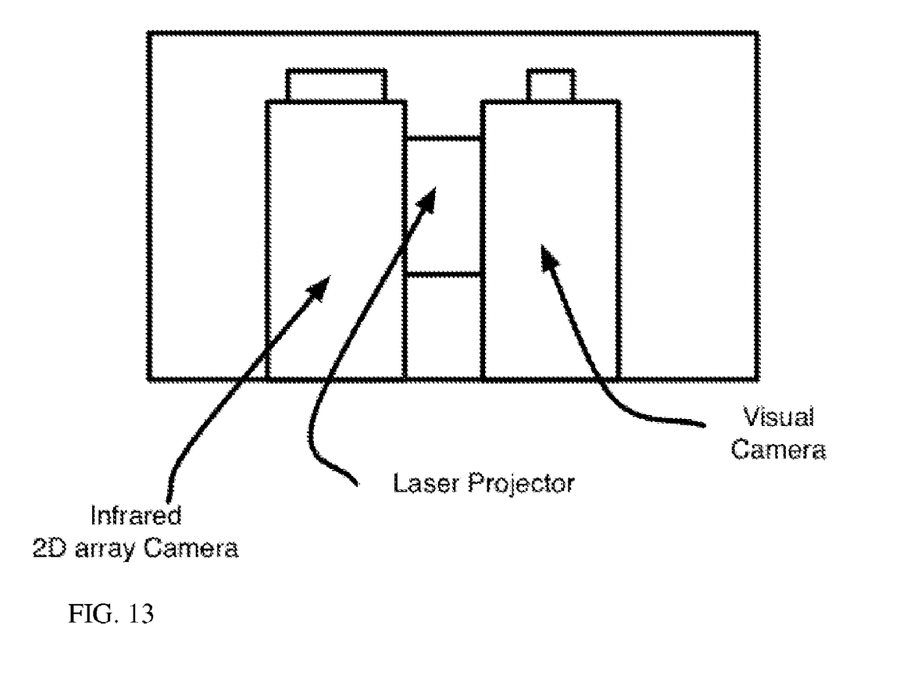
FIG. 13 is a schematic of a visual infrared laser assembly of the invention.
Figure 14:
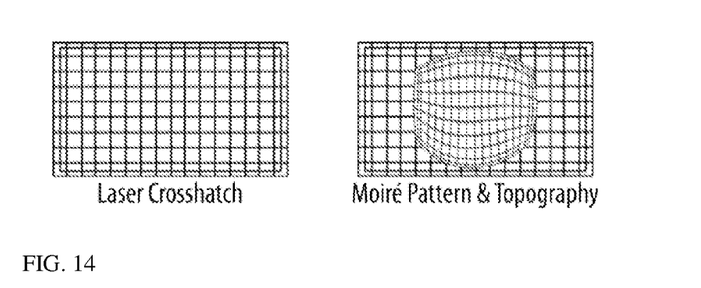
FIG. 14 depicts a crosshatch pattern of a Moire' pattern.
Figure 15:
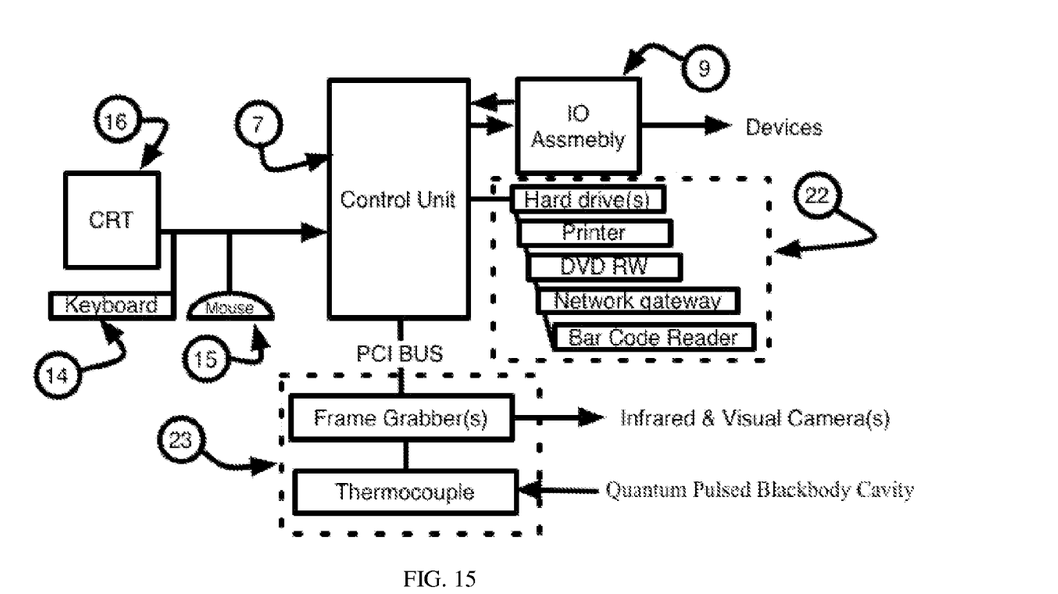
FIG. 15 is a hardware schematic of the invention.

After initial system calibration (approximately 5 seconds) the laser portion of the VIL assembly (6) (FIG. 13) turns on and initiates the crosshatch pattern. The laser projects a crosshatch pattern onto the surface of the subject, in this case on the breast (FIG. 14 of crosshatch pattern projected on non linear curved surface). The visual data will later be combined with other data in the final processing to correct for loss of infrared energy due to angles of emittance.

Figure 16:
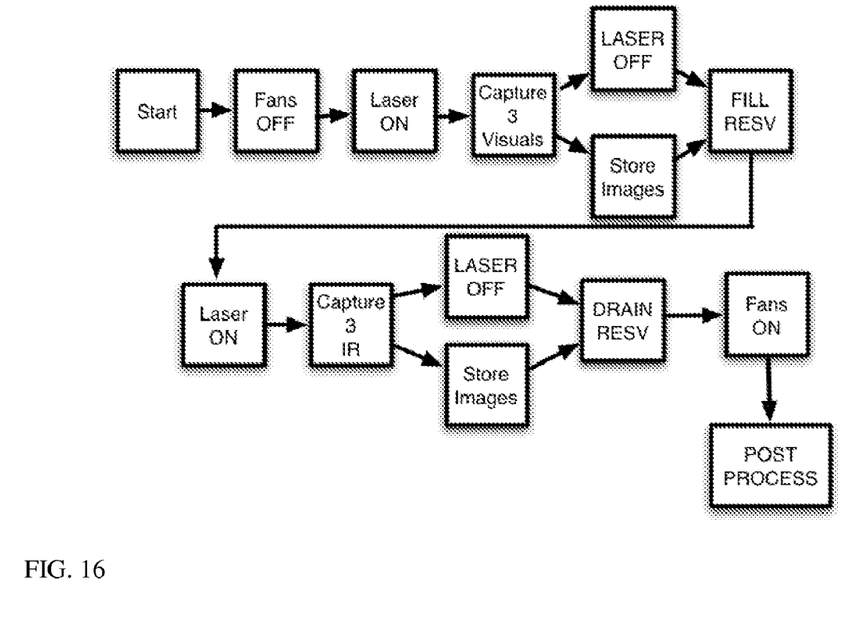
FIG. 16 depicts a process of operational steps.

While the laser is projecting the crosshatch pattern onto the subject surface the control unit (7) initializes the visual camera of the VIL assembly (6) to capture and store three frames of visual data (e.g., at 60 milliseconds apart) from the visual camera. The process steps are illustrated in FIG. 16. This data contains the geometry necessary for post processing.

The three frames are stored on a hard-drive contained within the control unit (7). The data that is derived during these captures provide the Moiré pattern that is the result of the laser crosshatch projection bending over the curvatures of the breast. These three frames are used to calculate projected infrared energy emitted from the object by correcting for the loss of energy due to the angles. Immediately following the crosshatch images the control unit will capture three sequential infrared images at intervals (e.g., 60 milliseconds apart) and store these images on a hard drive for post processing.

The control unit (7) will turn on the chiller pump (3) and fill the reservoir (2) with liquid at a temperature of between 34 to 40 degrees F. The subjects' hand and wrists are immersed in the liquid. The cold liquid on the subjects hand and wrists have a biophysical effect on the chest cavity of the body. The effect of this cooling stimulus causes the blood vessels in the area of the chest to restrict and an overall cooling effect of the chest occurs due to decrease blood flow. In the case of tumors/cancer the blood vessels that are feeding these cells have a unique property of not having any nerve cells therefore they cannot contract as the blood vessels feeding normal tissue.

After a short period of time the control unit (7) initiates the laser crosshatch pattern and three images are captured and stored in the same method of the initial sequence of crosshatch images. The control unit (7) then turns off the laser and visual camera and captures three infrared images at 60 milliseconds intervals and stores these images. This completes the raw data acquisition and the control unit (7) signals the chiller (3) to open the drain and remove the liquid from the reservoir (2). The control unit (7) turns on all the fans (19) and opens the shutters of the fans to stabilize the imaging section for the next screen.

Data acquisition flow, excluding the calibration process, is illustrated in flow chart 1.00. Flow chart 1.00 defines the sequence of events for the data acquisition of the raw thermal data, the geometry for thermal data correction.

Figure 17:
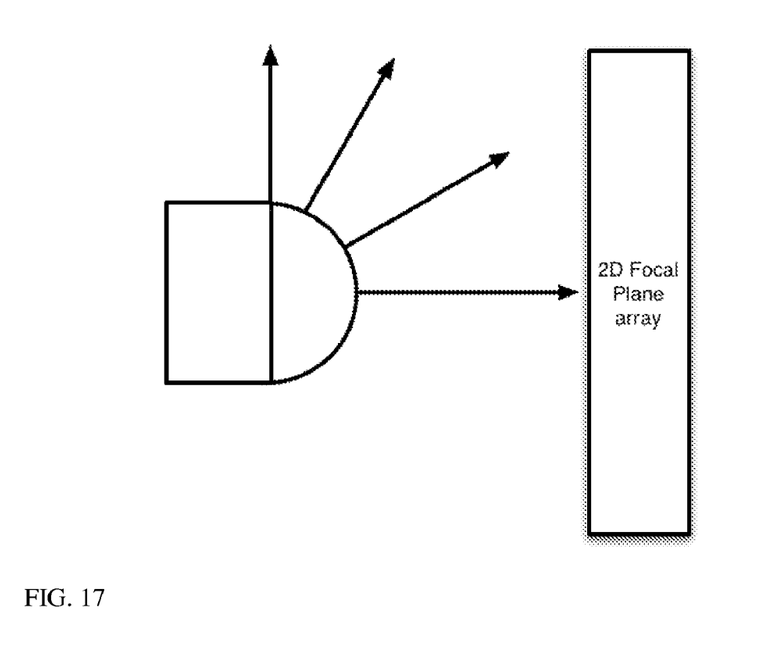
FIG. 17 depicts the angle of thermal emissivity.

As mentioned, curved surfaces, particularly surfaces greater than 45 to 50 degrees, appear to have less thermal energy than the surface that is normal to the camera even though the temperature is the same. This is due to the angle of emitted radiation as seen in FIG. 17.

Historical screening over a period of years or months require that from image to image and date to date all thermal values must be accurate. The infrared camera is calibrated for biophysical imagining and each screen the camera is calibrated to a known standard. Within the field of view of the infrared camera a small blackbody target is detected to insure repeatable screening data.

The enclosure (1) construction combined with the thermal uniformity of the enclosure eliminates the effects of stray radiation and possibilities of false temperature reading from the area of interest that is being acquired. By employing the spectral wavelength of thermal emissions of humans and continuously monitoring the calibration at the same wavelength this provides for accurate temperature measurements and necessary correction, if required. The incorporation of interference patterns projected by the laser insures that angular infrared radiation losses are reconstructed to their actual temperatures. All these aforementioned factors combined provides for an accurate thermal map of the area of interest. By controlling these known factors, this leaves the random noise generated in all 2D thermal arrays as the last variable to acquiring an accurate thermal map.

A major short coming of traditional mammograms is that only a portion of the breast can be imaged and early signs of breast cancer cannot be seen in the area of the chest wall above the breast as in the case of Infiltrating Lobular cancer. A major advanced of the topographic optical infrared tomgraphy system (100) in the area of breast cancer screening is that this area is included when performing the screen.

Figure 18:
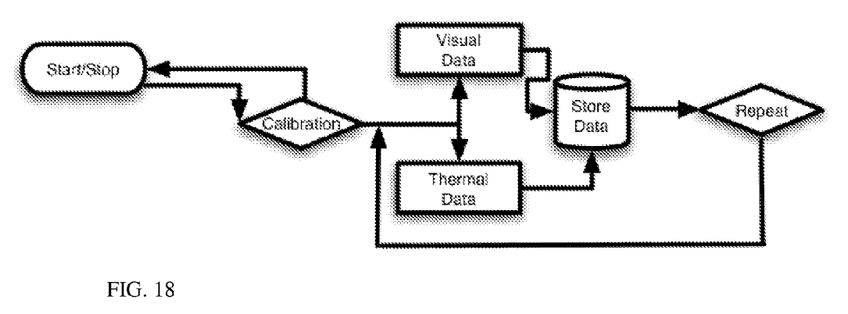
FIG. 18 depicts operation steps of the data acquisition of the invention.

With the subject in place for the data acquisition process, the system (100) performs an initial calibration by reading the blackbody (24) cavity. Upon successful calibration the system (100) projects a crosshatch pattern using the laser of the VIL assembly (6) on the area being imaged the visual camera of the VIL assembly (6) is employed to store this visual data while concurrently acquiring multiple thermal images of the area of interest and storing the thermal data. Optional stimulus may be applied and the process is completed resulting the pre and post visual and thermal data (FIG. 18)

Figure 19:
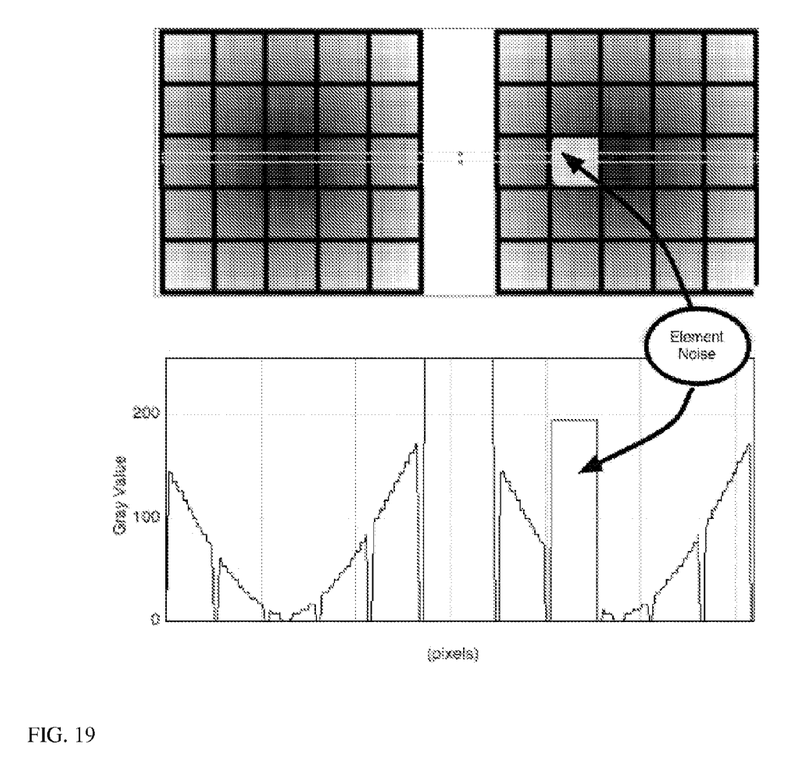
FIG. 19 depicts thermal noise.

All thermal images contain thermal array noise. With almost certainty some of the elements of the thermal 2D array may sparkle or not refresh properly during each frame capture. These anomalies generate thermal noise that is unlike other CCD image noise, as displayed in FIG. 19.

To remove the thermal noise each thermal image is scanned for any step functions that do not meet the criteria of thermal dynamics surface conduction patterns, i.e. the thermal value from a 2D element array, element 2, 3 versus element 1, 3 (As displayed in FIG. 19) cannot exceed a delta of 1 degree due to the conduction (v=0.5) properties of skin. A noise correction algorithm then performs a nearest neighbor using a Gaussian correction convolution. Each element that is corrected is stored for validation. This correction is performed on all sequential thermal images. These thermal elements are then analyzed insuring the variance is within the predicable surface conduction pattern and each element and corrections are applied and the images are then averaged into a single thermal image.

Figure 20:
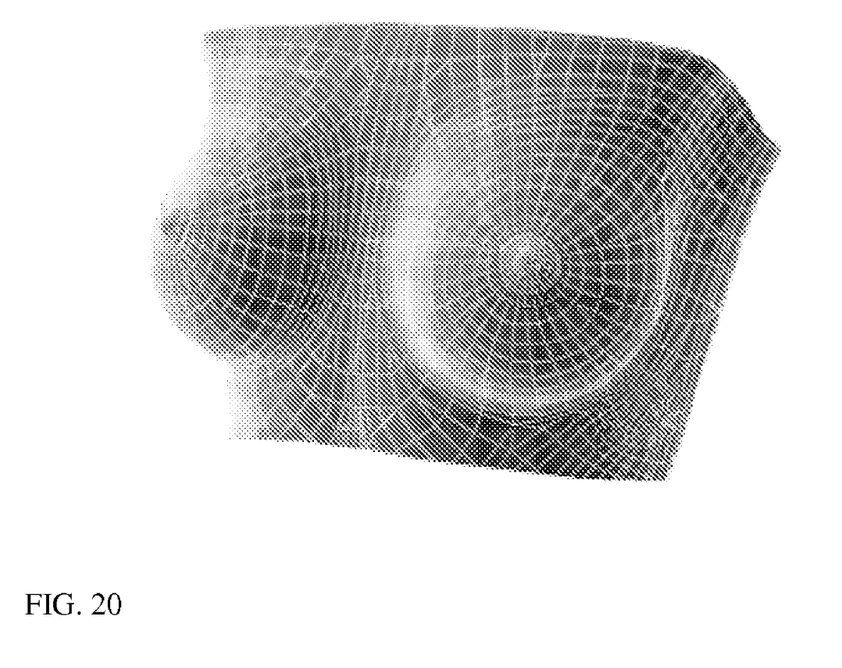
FIG. 20 depicts a thermal array over breasts.

The visual data array image(s) and the thermal data array images(s) are aligned and the control unit performs geometric calculation based on the interference pattern (visual image) calculating the angles of emission for each element in the visual 2D array image. The data calculated constructs a 3D wire frame of the area that has been imaged (FIG. 20).

Figure 21:
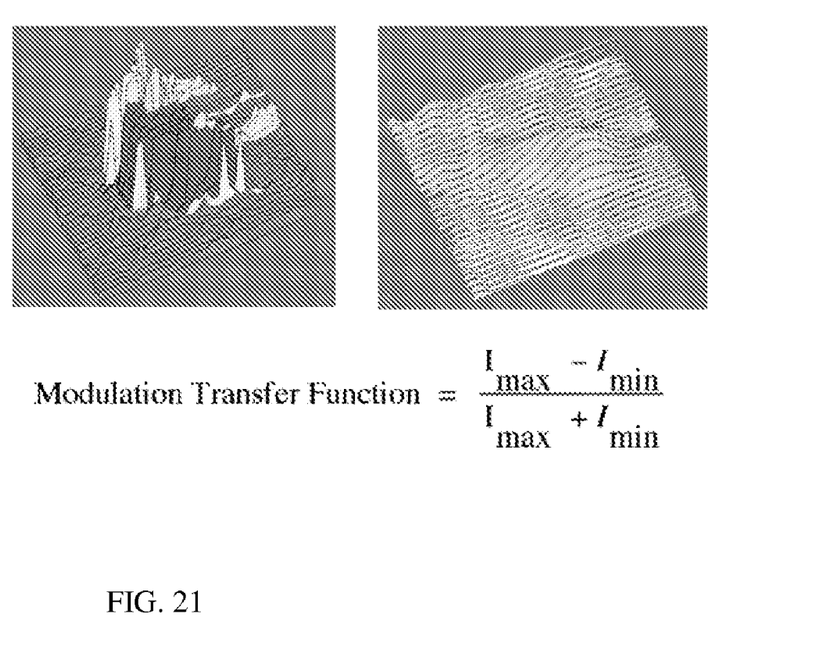
FIG. 21 depicts a modulation transfer function graph.

This data from the thermal 2D array is then surfaced mapped via coordinate geometry for each array element. Thermal variations due to angles of radiation are corrected and the result provides the user a 3D thermal image for analysis. When stimulation is applied during an imaging procedure the same process is performed as described for the initial set of data (FIG. 21).

Unlike x-ray images, that indicate densities, this provides unique analysis techniques based on thermal data to aid the reader in making a diagnostic. There are seven basic types of breast cancer: Ductal Carcinoma in-situ, Infiltrating Ductal, Medullary Carcinoma, Infiltrating Lobular (difficult to diagnose with traditional screening procedures), Tubular Carcinoma, Mucinous Carcinoma and Inflammatory Breast Cancer. The system (100) incorporates biophysical algorithms and pattern recognition that aids the user in early detection of these conditions. Specifically, the algorithms for cancer are based on the angiogenesis associated with cancer cells. Biophysical surface (skin) thermal properties are a direct indication of events beneath the surface and the principal factor for cancer detection is founded on the fact the blood flow is the driving force of tissue temperature changes.

The system incorporates biophysical algorithms that aid in determining if the area of concern is malignant or benign. In the diagnostics of breast cancer there is differing methodologies for diagnosing the subject. One such methodology is the symmetry of the right breast versus the left breast. It is envisioned that the diagnostic section of the system (100) can include symmetry analysis algorithms as well as many traditional techniques, in algorithm form, that are not unique to the diagnostic of breast cancer.

Figure 22:
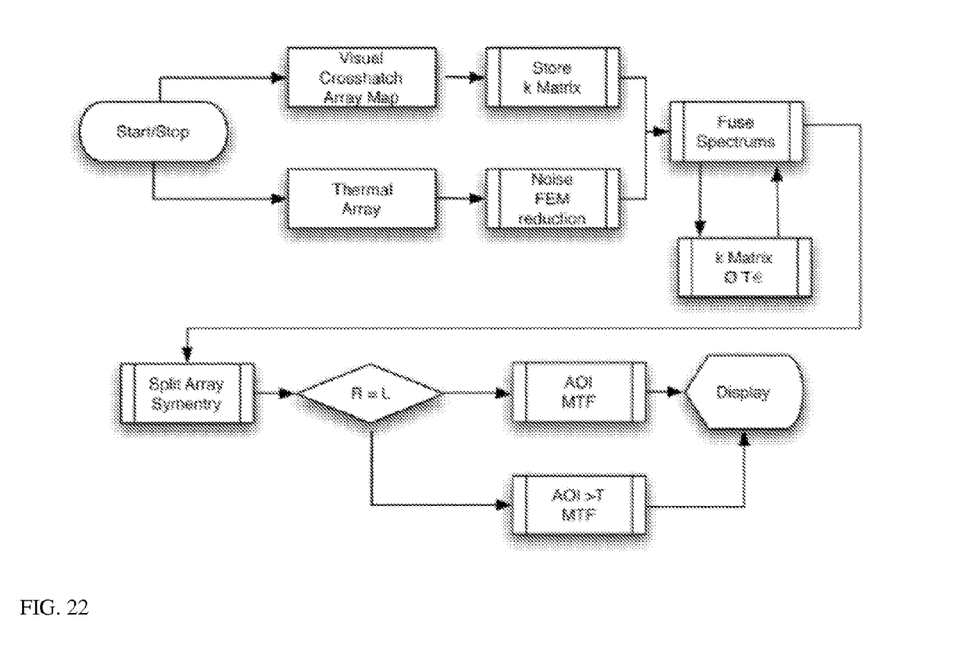
FIG. 22 depicts operational steps of the invention.

The topographic optical infrared tomography system (100) can incorporate neural networks that analyze an image of a suspected abnormal region by performing a boundary thermal analysis. When applying this boundary analysis and the thermal signatures derived the system weights this boundary condition and predicts if the area of concern is benign or malignant. The system (100) can employ a pattern analysis (Modulation Transfer Function) of the observed area integrated with a Laplace equation for thermal distribution of surface properties. FIG. 22 illustrates the Modulation Transfer Function of two abnormal tissues that have been modeled and identified. The thermal/mass image on the left clearly displays a thermal activity surrounding the AOI, while the thermal/mass image on the right indicates no activity.

$$\text{Modulation Transfer Fuction} = \frac{I_{max} - I_{min}}{I_{max} + I_{min}}$$

Within the analysis capabilities of the system, numerous ductile, vascular and thermal patterns scan the image to identify areas of concern. The various screening techniques have their advantages and well as their disadvantages and it is contemplated that combining techniques can provide a more complete diagnostic. For example, the system (100) saves the acquired data in both image raw format and in a DICOM image format and can incorporate algorithms that allow the user to input x-ray DICOM images and the system and merge the x-ray data with the thermal data.

With respect to FIG. 22, there is provided a flow chart of process steps of the invention. The visual camera combined with the crosshatch laser acquired an array and integrates into a 3D coordinate geometry thermal finite element model (FEM) stored in a k matrix. In parallel or concurrently, a thermal picture is taken, via thermal array, the infrared noise (FEM) reduction is performed on the thermal image based on empirical K (thermal conductivity) of the epidermis. These thermal and visual mathematical arrays are stored as 3D element models and stored into k matrix model (3D coordinate geometry) and the fused visual and infrared arrays into a 3D thermal model. Thermal adjustment for angles of radiation Ø, emissivity € and thermal conductivity T calculated and appended to the 3D element model (fused array). The fused array 3D FEM is divided in sections by symmetry, for example the right and left breast arrays, and stored. Areas of the model with higher thermal values are edged processed and the MTF is performed. The respective area and volume of the right and left sections are evaluated to determine if equivalent and if not, the sections are weighted for purposes of the MTF. The FEM is contoured into a thermal image using the MTF and areas of interest (AOI) are displayed to the user. Although the discussion focuses on breast cancer screening the same methodology and techniques are associated with other forms of cancer such as liver and prostate to site two. Screening processes and algorithm procedures for various organs and skin are selectable by the user.

The system (100) also includes an Infrared Diagnostic Exploratory Algorithm Sequencing (termed: IDEAS). IDEAS can allow a user to design a specific screening process by selecting icons that represent a specific process built unique for defined procedures that are executable.

IDEAS expands the capabilities of the system to a multiple screening applications. IDEAS allow the user to perform research and exploration of many forms of biophysical imaging by employing the systems sophisticated biophysical thermal algorithms, mathematical processing convolutions and three-dimensional modeling functions. For example, a graphical user interface can be provided for defining a procedure for a burn victim where an image of healthy tissue boundary can be enhanced. IDEAS can be operably associated with a modular database of functions and procedures for rapid prototyping, development and exploratory research. This system (100) can be used for small animal testing.

IDEAS can be configured to permit a user to select procedural items (which can appear as icons on a display) to be performed for a particular screening. Each icon contains a dialog box that allows the user to define variables that are associated with the procedure. For example, the ICON "ACQUIRE IMAGE" can have an associated dialog box that would allow the user to select either the visual camera or the thermal imaging camera.

The system (100) is a non-invasive imaging technique that images properties of biological tissue. Measurements of metabolic activity as diffused through tissue can be used to calculate and reconstruct images of surface and internal biophysical events in a three-dimensional mode. The design allows for imaging the entire human body, tissue samples as well a small animal testing. As a screening device for a specific procedure the system screening time is equivalent with traditional methods and being totally digital eliminates any environmental concerns such as chemicals necessary to development of an image.

In summary, thermographic screening has the benefit of being a totally passive technology however the current techniques and methodologies overlook the need for a controlled environment, emissivity corrections and actual tissue relating to body mass. Another deficiency of thermographic imaging is that infrared radiation radiates principally only at angles normal to the surface when viewed by the thermal array. Without multiple images of the area being imaged and repositioning the thermal array, thermal acquisition errors result due to the off angle of the energy being emitted. Depending on the geometry of the area being imaged the off angle radiation can be substantial. This is notable in examination of the mammary gland which is metabolic and there is an increase thermal activity during the menstruation cycle.

The present system (100) is a non-invasive imaging technique that can image properties of biological tissue. Measurements of metabolic activity as diffused through tissue can be used to calculate and reconstruct images of internal biophysical properties. The migration and diffusion of energy transfer through tissue is a function its physiological state and tissue properties that can display images of physiological parameters, which can be early markers of tumor/cancer development. Cancerous regions within normal tissue display substantially different physiology from normal tissue due to their primitive cell physiology. These abnormal regions have angiogenesis and higher degrees of metabolic rates when compared to normal tissue. The physiological differences will result in a change in thermal activity that can be detected and measured in tomographic data. Thermal fluid dynamics modeling combined with topographic correction modeling of the surface a propagation of thermal activity in tissue can be used to calculate maps of thermal changes within the breast, and therefore physiological maps of metabolic rates can be displayed with accuracy in an image for analysis.

The image data acquired is not limited to the screening of cancer. The image data combined with selected embedded procedural algorithms can be used for the analysis of aiding the grafting of skin for burn sufferers, reducing the pueblo effect aiding in pharmaceutical drug chemical reaction analysis and similar biophysical functions.

In the case of burn sufferers where skin grafting is necessary the largest risk of this procedure is the amount of grafting required. The surgeon performing this procedure determines what is healthy tissue versus dead tissue without any basis that a visual indication. A controlled thermal image of the area of the burn, using the techniques and methodology of the system (100) can provide an image of living tissue versus dead tissue. In the case of pharmaceutical companies testing new drugs this can reduce their test time by acquiring biophysical data in the area that the drug should be interacting. This allows for the pharmaceutical company to validate the effects of their new drugs with data that measures the effects. This technique could reduce the new drug time to market duration as well as saving millions of dollars of clinical trails and studies.

The system (100) incorporates acquisition and mapping hardware and software within a thermally controlled environment with advanced imaging devices employing various processing algorithms. These algorithms not only provide for image enhancements the software provides artificial intelligence of detailing and highlighting suspected area of concern(s) that aids the reader of the data in analyzing the acquired data.

The above described embodiments are set forth by way of example and are not for the purpose of limiting the present invention. It will be readily apparent to those skilled in the art that obvious modifications, derivations and variations can be made to the embodiments without departing from the scope of the invention. Accordingly, the claims appended hereto should be read in their full scope including any such modifications, derivations and variations.

The invention claimed is:

1. A topographic optical infrared tomography system for biophysical imaging a living body part, which comprises:
   a thermal camera operably disposable adjacent the living body part for obtaining thermal data readings from the living body part; and
   a computer based device equipped with hardware and software operably connected to said thermal camera, wherein said computer based device employs a predetermined wavelength corresponding to a healthy living body part for use in correcting thermal emissivity variations due to varying angles of thermal emittance in said thermal data readings to provide corrected 3 dimensional thermal data, and wherein said hardware includes a laser for projecting a beam over the living body part to generate Moiré surface patterns and said software utilizes Moiré surface patterns for the correction of angular thermal radiation of curved surfaces of the living body part.

2. The system of claim 1, further comprising an imaging compartment configured to receive the living body part therein and wherein said thermal camera is operably disposed in said compartment.

3. The system of claim 2, wherein said compartment includes mirrors operably disposed in said compartment to aid in obtaining said data.

4. The system of claim 2, wherein said imaging compartment is coated with conductive paint.

5. The system of claim 1, further comprising a phase change material that has the ability to quickly absorb a predefine temperature extreme.

6. The system of claim 1, further comprising an LED blackbody member for calibration configured for the living body thermal imaging and wherein energy generated therefrom is a predetermined frequency, said predetermined wavelength and an intensity controlled by a duty cycle controller operably connected thereto.

7. The system of claim 1, wherein said hardware and software for acquiring visual 2D image data and thermal 2D array data and manipulating said 2D data into a thermally corrected data and constructing a 3D image from said thermal corrected data.

8. The system of claim 1, wherein said software is configured for analyzing said thermal corrected data and generating one of an indication of a normal or an abnormal condition.

9. The system of claim 8, wherein said software includes a spatial transfer function to generate said indication of condition.

10. The system of claim 8, wherein said software includes a neural network to generate said indication of condition.

11. A method of obtaining thermal data, the method comprises the steps of: (a) obtaining thermal data readings from a living body part using hardware and software for acquiring visual 2D image data and thermal 2D array data; and (b) correcting thermal emissivity variations and thermal radiation losses due to varying angles of thermal emittance in said thermal data readings to provide corrected thermal data by manipulating said 2D data into a thermally corrected data and constructing a 3D image from said thermal corrected data and which employs a computer based device using a predetermined wavelength corresponding to a healthy living body part, which further comprises in step (b) employing a laser to generate a laser Moiré pattern on the living body part and employing a visual camera to capture a visual image data of said laser pattern and the living body part.

12. The method of claim 11, further comprises in step (a) employing a thermal camera adjacent the living body part.

13. The method of claim 11, wherein the correcting of said thermal data is performed as a function of said visual image data.

14. The method of claim 11, further comprising step (c) providing an environment for minimizing thermal reflection prior to performing the step (a).

15. The method of claim 11, further comprising in step (c) employing said corrected thermal data to generate an indication of a normal or an abnormal condition of the living body part.

* * * * *